United States Patent [19]
Rappaport

[11] Patent Number: 5,470,352
[45] Date of Patent: Nov. 28, 1995

[54] BALLOON ANGIOPLASTY DEVICE

[75] Inventor: Carey M. Rappaport, Newton, Mass.

[73] Assignee: Northeastern University, Boston, Mass.

[21] Appl. No.: 145,878

[22] Filed: Oct. 29, 1993

[51] Int. Cl.[6] .............................. A61B 17/36; A61N 5/02; A61M 25/10
[52] U.S. Cl. ........................ 607/101; 607/156; 606/33; 606/194
[58] Field of Search .................. 606/33, 194; 607/100, 607/101, 102, 154, 156; 128/653.1

[56] References Cited

U.S. PATENT DOCUMENTS

| | | | |
|---|---|---|---|
| 4,445,892 | 5/1984 | Hussein et al. | 604/101 |
| 4,643,186 | 2/1987 | Rosen et al. | 607/156 |
| 4,817,635 | 4/1989 | Joines et al. | 607/101 |
| 4,825,880 | 5/1989 | Stauffer et al. | 128/804 |
| 4,841,988 | 6/1989 | Fetter et al. | 128/804 |
| 4,860,752 | 8/1989 | Turner | 128/422 |
| 4,924,863 | 5/1990 | Sterzer | 606/27 |
| 4,945,912 | 8/1990 | Langberg | 128/642 |
| 4,961,422 | 10/1990 | Marchosky et al. | 128/401 |
| 4,967,765 | 11/1990 | Turner et al. | 128/785 |
| 4,969,890 | 11/1990 | Sugita et al. | 606/192 |
| 4,974,587 | 12/1990 | Turner et al. | 128/399 |
| 4,989,601 | 2/1991 | Marchosky et al. | 128/399 |
| 4,998,932 | 3/1991 | Rosen et al. | 606/29 |
| 5,057,106 | 10/1991 | Kasevich et al. | 606/33 |
| 5,122,137 | 6/1992 | Lennox | 606/40 |
| 5,129,396 | 7/1992 | Rosen et al. | 128/653.1 |
| 5,135,487 | 8/1992 | Morrill et al. | 604/96 |
| 5,150,717 | 9/1992 | Rosen et al. | 128/804 |
| 5,330,518 | 7/1994 | Neilson et al. | 607/101 |

FOREIGN PATENT DOCUMENTS 9210932  7/1992  European Pat. Off. ............... 607/154

OTHER PUBLICATIONS

A Helical Microwave Antenna For Welding Plaque During Balloon Angioplasty by Carey M. Rappaport and Ping Liu, NIH Grant R03 RR05333-01, Nov. 1, 1993, pp. 1-3.

*Primary Examiner*—Krista M. Zele
*Attorney, Agent, or Firm*—Weingarten, Schurgin, Gagnebin & Hayes

[57] ABSTRACT

A balloon angioplasty device includes a microwave antenna, a catheter and a transmission line disposed through the catheter and coupled to the antenna. The device further includes a balloon coupled to the catheter and a mode filter disposed about the antenna.

20 Claims, 6 Drawing Sheets

BALLOON ANGIOPLASTY DEVICE

This invention was made with Government support under Grant 1RO3 RR0533301 awarded by the National Institute of Health. The Government has certain rights in this invention.

FIELD OF THE INVENTION

This invention relates to angioplasty techniques and more particularly to microwave antennas used in balloon angioplasty techniques.

BACKGROUND OF THE INVENTION

As is known in the art, percutaneous transluminal coronary angioplasty or simply balloon angioplasty is a technique in which arteries obstructed by plaque build up are cleared. One problem with this technique however is that abrupt reclosure and gradual refilling of the artery typically occurs in about 17–34% of those cases in which the technique is used.

As is also known, laser radiation has been used in conjunction with balloon angioplasty to deliver power to plaque and weld it in place. The laser radiation technique is primarily a thermal process, dependent on maintaining an elevated plaque temperature level in the range of about 95° to 143° C. One problem with this technique, however, is that it is relatively difficult to distribute the laser energy uniformly around the plaque. Furthermore it is difficult to apply the correct intensity to heat plaque without overheating healthy artery tissue.

Another approach used to deposit power in conductive media is microwave irradiation. Radio-frequency (RF) energy including microwave energy may be used to non-invasively generate heat within tissue volumes. Although there are wide variations in the types of biological tissue, the electrical characteristics of biological tissue may generally be grouped into two classes. The first class includes high-water-content tissue (HWC), including muscle, organ, and blood and blood vessel walls. The second class includes low-water-content tissue (LWC), including fat and bone. Atherosclerosis plaque which collects on the inner walls of blood vessels is generally composed of lipids and calcium particles, and thus may also be considered LWC. The dielectric constants and conductivities of HWC and LWC tissue classes vary directly, although non-linearly, with frequency. Generally, HWC values are several times greater than LWC values.

With such large differences in electrical characteristics between LWC and HWC tissue, radiation may be strongly reflected at tissue boundaries, and power dissipation depends on the angle at which the incident wave impinges the boundary between the LWC and HWC tissue. The tangential electric field component must be continuous across the boundary between the LWC and HWC tissue, but the component of the electric which is normal to the boundary is much smaller in the HWC tissue. Dissipated power P may be computed $$P = \frac{\sigma|E|^2}{2},$$

in which E corresponds to an electric field intensity and $\sigma$ corresponds to electrical conductivity. The electrical conductivity is greater in HWC tissue than LWC tissue, thus, the power P deposited by a normally-polarized electric field on the HWC tissue may be significantly less than in the LWC side.

On the other hand, the tangential electric field polarization is continuous across the boundary and will deposit approximately one order of magnitude more power on the HWC side. Conventional microwave-assisted balloon angioplasty devices tend to generate an electric field having an electric field polarization which is primarily tangential to the artery wall. Consequently, conventional microwave balloon angioplasty devices may overheat healthy tissue. Thus it would be desirable to provide an antenna which may be used in balloon angioplasty devices and which does not overheat healthy tissue.

SUMMARY OF THE INVENTION

In accordance with the present invention a balloon angioplasty device includes an antenna, a balloon disposed about the antenna and a mode filter disposed about the antenna for minimizing a particular electric field component radiated by the antenna. With this particular arrangement, a balloon angioplasty device which heats plaque build up in an artery but which does not heat surrounding healthy tissue is provided. The mode filter may be provided as a plurality of conductive strips disposed on an inner or outer surface of the balloon. The mode filter may include at least one Z-shaped conductor or alternatively may include a plurality of conductive strips disposed to provide a plurality of interdigitated strip conductors. The antenna may be provided as a helical antenna which radiates an electric field. The mode filter prevents particular electric field components from undesirably heating healthy body tissue while allowing other electric field components to heat plaque build up. After the plaque is heated the balloon, mode filter and antenna elements are removed from the artery. Making use of favorable normal electric field polarization, waves which propagate down the axis of a blood vessel with a radially-polarized electric field may deposit more power in the plaque layer then in the healthy artery wall, thus minimizing the risk of damage to the healthy artery wall due to overheating. The microwave antenna heating device of the present invention may be used in conjunction with balloon angioplasty to alleviate reclosure and restenosis. The fields radiated by the helical antenna may be optimized in frequency and pitch angle to establish power deposition patterns which preferentially heat plaque while not significantly heating healthy artery wall tissue. This system is less complex and costly than laser welding. It is also inherently safer since the microwave fields propagating in lower conductivity plaque tend to reflect from the higher conductivity muscle boundaries, thus, remaining confined to the plaque layer.

BRIEF DESCRIPTION OF THE DRAWINGS

The foregoing features of this invention as well as the invention itself may be more fully understood from the following detailed description of the drawings in which.

DESCRIPTION OF THE PREFERRED EMBODIMENTS

Figure 1:
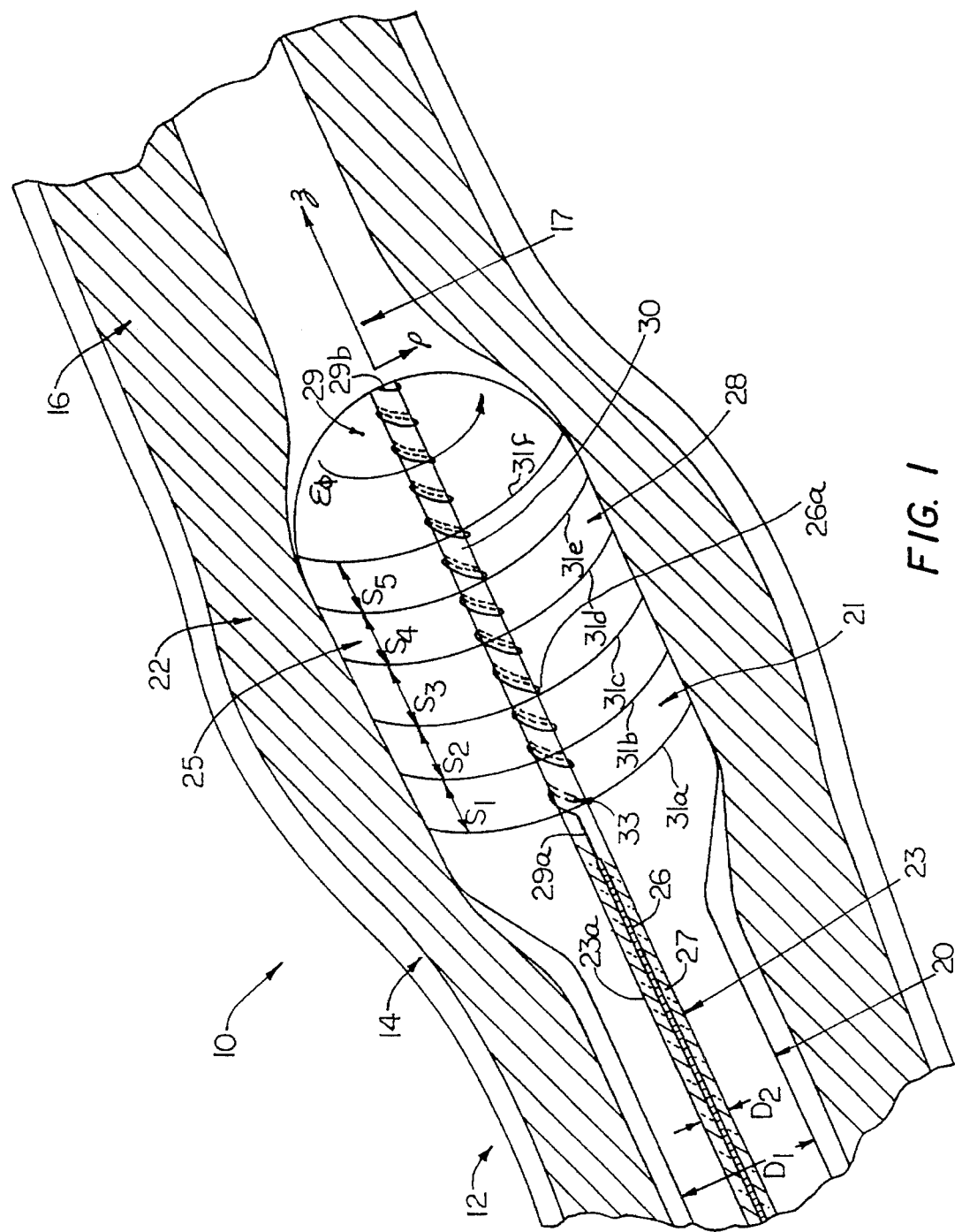
FIG. 1 is a partial cross-sectional view taken along a longitudinal axis of a portion of an artery having a balloon angioplasty device disposed therein.

Referring now to FIG. 1, a balloon angioplasty device 10 is shown disposed in a portion of an artery 12. Artery 12 includes an artery wall 14 having plaque 16 deposited on a surface thereof. Plaque 16 narrows the diameter of artery 12 such that the flow of blood 17 is restricted within the artery 12.

Balloon angioplasty device 10 includes a catheter 20 having a balloon 21 coupled to a first end thereof. Balloon 21 may be inflated to widen artery 12. Inflation of balloon 21 may be accomplished by insertion of fluids. Such fluids are preferably provided having a relatively low dielectric constant and provide a minimum amount of attenuation to RF signals propagating therethrough. A preferable fluid is a perfluorocarbon liquid or the like. In some applications saline may also be used. Inflation of balloon 21 in artery 12 provides a region of compressed plaque 22.

A coaxial cable 23 having an outer jacket 23a and a center conductor 26 spaced by a dielectric region 27 is disposed through catheter 20 and extends into balloon 21. A portion of outer jacket 23a and dielectric 27 have here been removed to expose a portion 26a of center conductor 26. In response to electromagnetic energy fed through coaxial cable 23, exposed center conductor 26a radiates electromagnetic energy. Thus exposed center conductor 26a acts as an antenna 29.

Exposed center conductor 26a is here wound in a helix configuration to provide the antenna 29 as a helix antenna. An optional dielectric rod 30 is disposed through the center of the helical antenna 29. A first end 29a of antenna 29 is thus coupled to center conductor 26 of coaxial line 23. A second end 29b of antenna 29 may be terminated in either an open circuit, short circuit, or matched impedance characteristic. In an alternate embodiment, the helical antenna 29 may be provided as a printed circuit antenna formed by disposing a strip conductor 33 on a surface of the dielectric rod 30. The strip conductor 33 may be disposed on the dielectric rod via patterning or etching techniques well known to those of ordinary skill in the art.

Helical antenna 29 radiates electric fields $E_\rho$, $E_z$ and $E_\phi$ in the radial, axial and circumferential directions as is generally known. The direction of circumferential electric field $E_\phi$ is tangential to the boundary between plaque 16 and artery wall 14. Consequently, the circumferentially directed electric field component $E_\phi$ must be continuous across the boundary between plaque 16 and healthy artery wall 14. Thus circumferentially directed electric field component $E_\phi$ tends to deposit energy in both plaque 16 and in the surrounding healthy tissue 14. It would therefore be desirable to minimize the circumferentially directed electric field component which propagates through healthy artery wall 14.

The radially directed electric field component $E_\rho$, on the other hand, is normal to the boundary between plaque 16 and healthy artery wall 14. Because of the difference in the electrical characteristics including the relative dielectric constants between plaque 16 (i.e. LWC tissue) and the healthy artery wall 14 and surrounding muscle and organ mass (i.e. HWC tissue), the radially directed electric field component $E_\rho$ is much smaller in the HWC tissue than the LWC tissue and thus tends to deposit relatively little energy in the healthy tissue 14. It would therefore be desirable to not attenuate the radially directed electric field component $E_\rho$ while simultaneously minimizing the circumferentially directed electric field component which propagates through healthy artery wall 14.

Catheter 20 is here provided having a diameter $D_1$ typically in the range of about 0.1 inches to 0.5 inches. Coaxial cable 23 is provided having an outer diameter typically in the range of about 0.04 inches to 0.4 inches. Center conductor 26 is provided having a diameter $D_2$ typically in the range of about 0.02 inches to 0.2 inches. Antenna 29 is provided having a diameter $D_3$ typically in the range of about 0.08 inches to 0.4 inches and a length typically in the range of about 0.7 inches to 2.0 inches. The particular dimensions of catheter 20, coaxial cable 23 and antenna 29 may be selected according to a variety of factors including but not limited to the particular coronary artery being treated, the desired frequency of operation, the type of fluid used to inflate balloon 21, the pitch angle $\alpha$ of antenna 29, the cross sectional diameter of artery 12, the age of the patient, the percentage of vessel occlusion, the duration of desired heating, the duration of the entire balloon angioplasty procedure, the symmetry of plaque deposition, the nominal rate of blood flow and the like.

Balloon 21 is provided having an inner surface and an outer surface. Disposed on a first one of the inner and outer surfaces is a mode filter 28. Mode filter 28 is here provided from a plurality of electrically conductive strips 31a–31f generally denoted 31. Conductors 31 are here disposed in circumferential directions around balloon 21. Furthermore, each of conductors 31a–31f is provided such that it effectively appears as a continuous strip around balloon 21. Moreover, each strip 31a–31f is dimensioned and disposed such that circumferentially directed electric field components $E_\phi$ are tangential thereto and thus electric filed component $E_\phi$ vanishes when incident thereon.

Strips 31a–31f may be provided having a cross-sectional shape which is rectangular, square, or round, for example. Strips 31 may for example, be provided as conductive ribbons having a width typically in the range of about 0.0001 inch to 0.001 inch and a thickness typically in the range of about 0.0005 inch to 0.001 inch. Alternatively strips 31 may be provided having a circular cross sectional shape with a diameter typically in the range of about 0.0005 inch to 0.001 inch Strips 31a–31f are here spaced by distances $S_1$–$S_5$. Here the distances are shown to be equal and are typically in the range of about 0.04 inches to 0.5 inches. It should be noted however, that distances $S_1$–$S_5$ may be equal or unequal. That is, strips 31a–31f may be equally spaced along a surface of balloon 21 or alternatively in some applications strips 31a–31f may be unequally spaced. It should also be noted that the particular size, cross-sectional shape and spacing of conductors 31a–31f should be selected such that mode filter 28 minimizes the circumferentially directed electric field component $E_\phi$. The particular dimensions of conductors 31 will depend upon a variety of factors including but not limited to the frequency at which antenna 29 radiates.

Conductors 31a–31f may of course also be disposed in other patterns as will be discussed further below in conjunction with FIGS. 3 and 3A. Suffice it here to say that mode filter 28 may be provided in any pattern using any number of conductors selected to minimize a particular electric field component having a direction which is tangential to the boundary between plaque and healthy tissue and thus which propagates into and undesirably heats healthy tissue.

Figure 2:
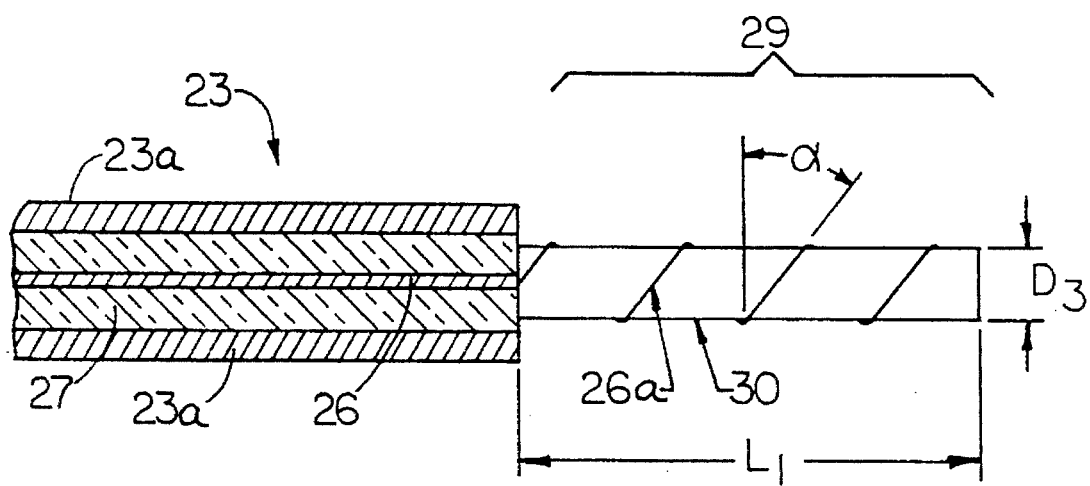
FIG. 2 is a partial cross-sectional view taken along a substantially central longitudinal axis of a coaxial cable having an antenna coupled thereto.
Figure 2A:
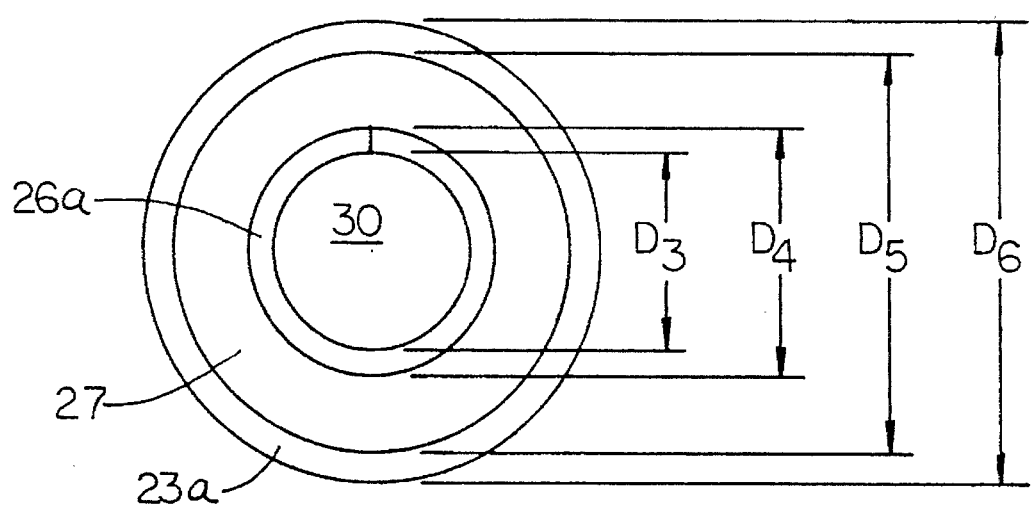
FIG. 2A is an enlarged end view of the antenna of FIG. 2.

Referring now to FIG. 2, antenna 29 including optional dielectric rod 30 is shown coupled to a portion of coaxial cable 23. Here catheter 20 (FIG. 1) and balloon 21 (FIG. 1) have been removed to more clearly show antenna 29. Conductor 26a maybe provided as a continuous portion of coaxial cable center conductor 26 as described above in conjunction with FIG. 1. Alternatively, however, it should be noted that conductor 26a which forms antenna 29 may be provided as a separate conductor which is coupled or joined to center conductor 26 using any technique well known to those of ordinary skill in the art.

Similarly, optional dielectric rod 30 may be provided as a continuous extension of dielectric 27 or alternatively rod 30 may be provided as a separate piece juxtaposed an end of coaxial cable 23. Rod 30 is provided to add structural support to antenna 29 and may be provided from any non-conductive material such as teflon rexolite, silicone or any other non conductor which is biologically benign. In some embodiments, the length L1 of antenna 29 may be selected such that rod 30 is not required for structural support.

In other embodiments, it may be desirable to form antenna 29 directly on a surface of rod 30 using positive or negative subtractive or additive etching processes or pattern deposition techniques. Thus, in such embodiments, antenna 29 would be electrically coupled to center conductor 26.

It should be noted, however, that the relative dielectric constant and diameter $D_3$ of rod 30 may be selected to maximize the likelihood that antenna 29 radiates a particularly desirable electric field configuration. Thus rod 30 may provide structural support for antenna 29.

A microwave energy source (not shown) excites helical antenna 29 causing antenna 29 to emit electromagnetic radiation. As mentioned above, helical antenna 29 preferably radiates in the axial mode. The microwave power source should thus be preferably selected to excite antenna 29 such that antenna 29 will provide an electric field having a substantially radial orientation at the interface between plaque 16 and tissue 14.

The particular electric field configuration radiated by helical antenna 29 is of course dependent upon a plurality of factors including but not limited to the radiation frequency, helix pitch angle $\alpha$, the relative diameter of the inflated balloon 21, the plaque-artery boundary, the dielectric constants of the inflating fluid, and the dielectric constant of the plaque and the artery wall. Thus by appropriate selection of operating frequency and helix pitch angle $\alpha$, for particular inner and outer plaque diameters and the inner artery wall diameter it is possible to establish power deposition patterns which preferentially heat plaque while not significantly heating healthy artery wall tissue. Thus, for a particular plaque thickness and artery wall size there exists an optimum pitch angle $\alpha$ and operating frequency for antenna 29.

As mentioned above in conjunction with FIG. 1, the diameter of antenna 26 may be selected according to a variety of factors including but not limited to the diameter of the artery wall, and the desired operating frequency. The diameter $D_3$ of dielectric rod 30 may be selected to provide helix antenna 29 with an appropriately dimensioned diameter.

Pitch angle $\alpha$ of antenna 29 is typically in the range of about 5 degrees to 60 degrees. By adjusting pitch angle $\alpha$ of helix antenna 29 as a function of wavelength in the plaque tissue, the radiated field can be polarized almost entirely radially.

A preferred frequency at which the mode filter 28 (FIG. 1) and helical antenna 29 may be used is typically about 8 Ghz. Other frequencies in the microwave frequency band may of course also be used. For example, in some applications a pitch angle of 17 degrees and an operating frequency of 1.8 GHz may be preferred. The particular operating frequency may be selected according to a variety of factors including but not limited to artery geometry, the percentage of occlusion and the coaxial cable loss. Thus for a particular artery geometry the pitch angle $\alpha$ and operating frequency may be varied to provide an optimum ratio of $E_\rho$ to $E_\phi$ electric field components which minimizes the amount of power delivered to the artery tissue and is effective to heat plaque. The values for $E_\rho$ and $E_\phi$ at a particular pitch angle $\alpha$ and operating frequency may be computed using techniques described in the appendix attached hereto and included as a part hereof.

Figure 3:
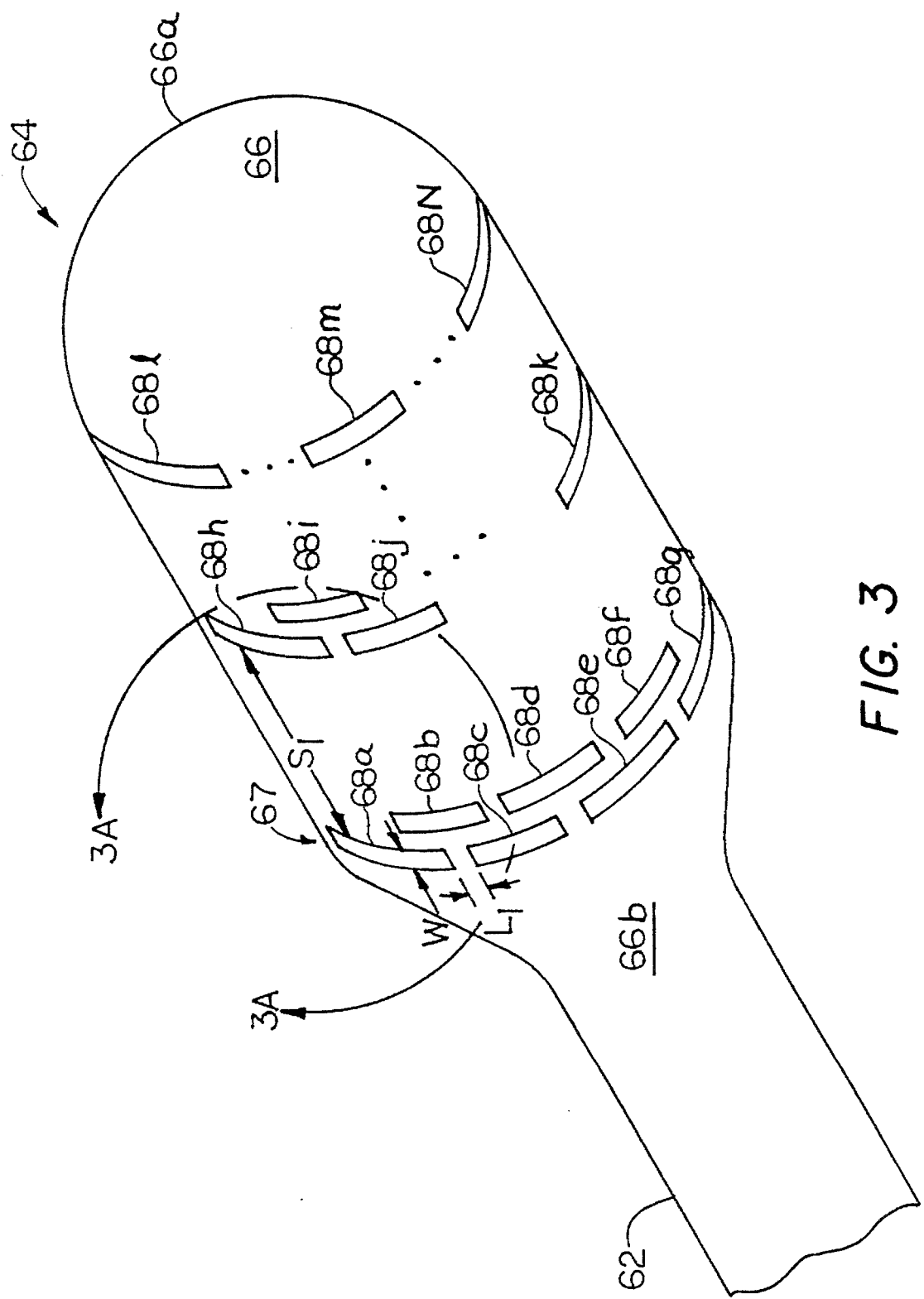
FIG. 3 is a perspective view of a balloon having a segmented mode filter disposed thereon.

Referring now to FIG. 3, a dilation catheter 60 includes a catheter portion 62 and a balloon portion 64. Balloon 64 may be provided from a thin highly flexible membrane 66. Balloon 64 is disposed to surround a microwave radiation source (not shown) which may be provided for example as antenna 29 (FIGS. 1 and 2). Balloon 64 should thus be provided from a material which is substantially transparent to electric fields radiated by a microwave radiation source.

Balloon 64 is provided having a closed end 66a and an open end 66b. The open end 66b of balloon 66 is disposed around a surface of catheter 62 to provide a fluid tight seal along the surface of catheter 62. Balloon 66 may be inflated or deflated by fluid pressure which may be either positive or negative and may be applied to the interior of balloon 66 by a channel (not shown) in catheter 62 as is generally known.

Balloon 66 here includes a mode filter 67 which is provided from a plurality of conductive strips 68a–68N generally denoted 68 disposed in an interdigitated pattern. Segments 68a–68g disposed along the circumference of balloon 66 form a conductive ring similar to conductor 31a (FIG. 1). That is, segments 68a–68g should appear to a circumferentially directed electric field component $E_\phi$ to be a continuous conductive strip on which the electric field $E_\phi$ vanishes. The particular width, length and pattern in which the segments 68a–68N are disposed should be selected to attenuate electric fields having a predetermined polarization.

By providing mode filter 67 as a plurality of interdigitated segments 68, balloon 66 is more easily able to deflate. Conductor segments 68 may be disposed on balloon 66 using conductive paint or by sputtering metal onto a surface of balloon 66 as is generally known. The thickness of conductive segments 68 is typically in the range of about 0.0005 inches to 0.001 inches.

Figure 3A:
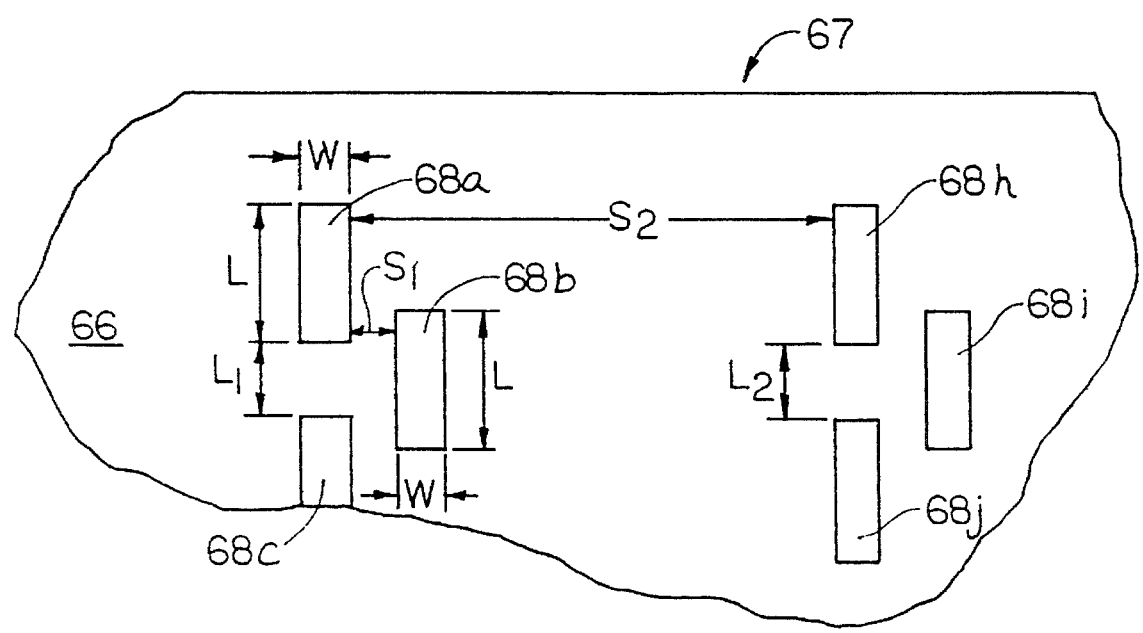
FIG. 3A is a plan view of a portion of the balloon and mode filter of FIG. 3.

Referring briefly to FIG. 3A, a representative one of segments 68, segment 68a is here provided having a rectangular shape having a length L and a width W. Segments 68a, 68c are spaced by a distance $L_1$ along a circumferential axis of balloon 21. Similarly, segments 68h, 68j are spaced by a distance $L_2$. Segment 68b is spaced in the axial direction a distance $S_1$ from segments 68a, 68b and segment 68h is spaced a distance $S_2$ from segment 68a. The particular spacings $L_1$, $L_2$, $S_1$, $S_2$ of segments 68 are selected to provide a mode filter 67 which minimizes an electric field component in a particular direction.

Referring again to FIG. 3, conductive segments 68a–68N are shown having a rectangular shape. It should be noted that conductive segments 68a–68N alternatively may be provided having a circular cross-sectional shape and a diameter typically in the range of about 0.0005 inch to 0.001 inch. Since it in this particular embodiment it is desirable to maximize the electric field in the radial direction $E_\rho$, segments 68 are disposed in a circumferential direction on a surface of the balloon 21. Thus, mode filter 67 here minimizes circumferentially directed electric field components $E_\phi$.

Figure 3B:
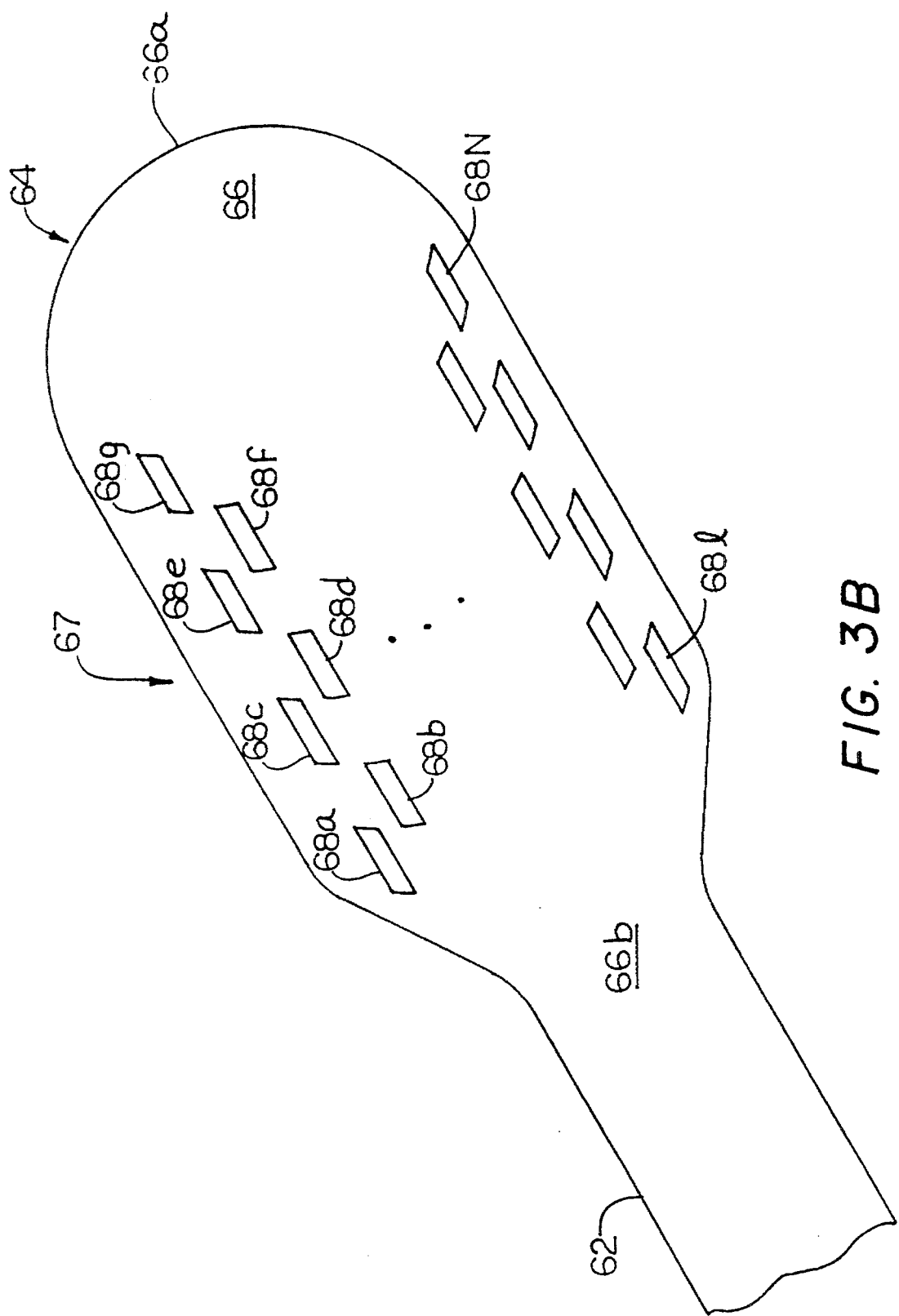
FIG. 3B is a perspective view of a balloon having a segmented mode filter disposed thereon.

However, if it were desired to minimize an electric field component directed in other the circumferential direction the segments 68 may be disposed in a different orientation. That is, if it were desirable to minimize an axially directed electric field component, then segments 68 would be disposed such that the longitudinal axis of each segment 68 would be directed in the axial direction as shown in FIG. 3B. Thus, as shown in FIG. 3B segments 68 are disposed along a longitudinal axis of balloon 66 rather than along a circumferential axis of balloon 66.

Figure 4:
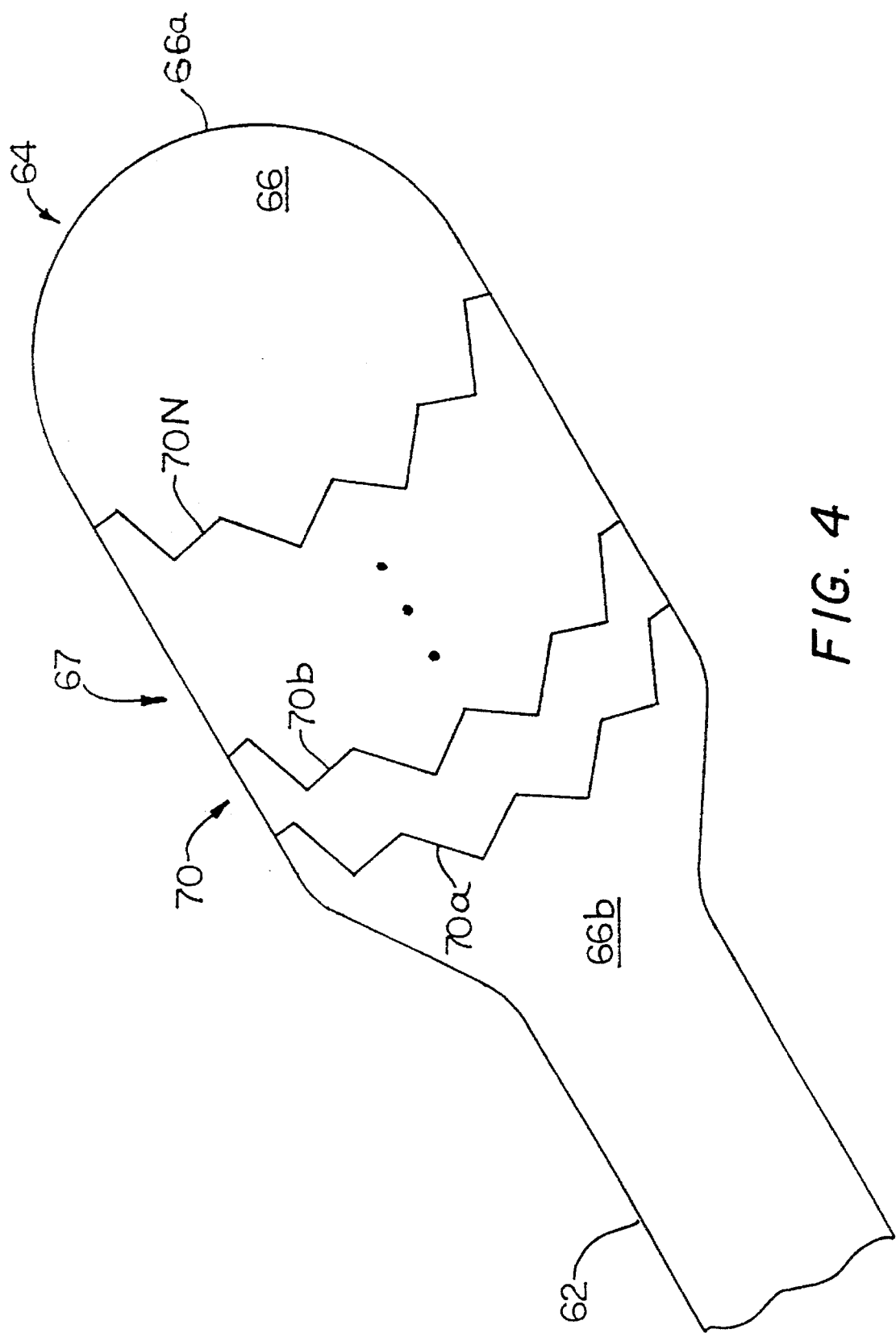
FIG. 4 is a perspective view of a balloon having a mode filter provided from Z-shaped conductors disposed thereon.

Referring now to FIG. 4, a mode filter 67' is provided from a plurality of conductors 70a–70N generally denoted 70 disposed on a surface of balloon 66 in a z-shaped pattern. Thus when balloon 64 deflates strip conductors 69a–69N collapse such that balloon 64 is able to fully deflate. However, when balloon 64 is fully inflated conductors 70 expand with the surface of balloon 64 and may become substantially straight similar to conductors 28 described in conjunction with FIG. 1 above.

Having described preferred embodiments of the invention, it will now become apparent to one of skill in the art that other embodiments incorporating the concepts may be used. For example, mode filter 28 has here been shown to be disposed on a surface of a balloon. It is apparent however that the mode filter need not be coupled to any particular structure but rather may be provided as a separate component in the balloon angioplasty device. For example, the mode filter may be coupled to and supported by rod 30 or antenna 29. In such an arrangement the mode filter conductors may be coupled to the rod or antenna via nonconductive struts for example. The particular manner and materials from which the mode filter is provided will be selected in accordance with a variety of factors including but not limited to the particular manufacturing techniques to be used. It is of course preferable to use low cost materials and manufacturing techniques while still providing a structurally reliable and electrically effective mode filter.

It is felt, therefore, that these embodiments should not be limited to disclosed embodiments but rather should be limited only by the spirit and scope of the appended claims.

What is claimed is:

1. A balloon angioplasty device for widening a path through which blood flows in an artery having plaque deposited on an inner wall thereof, the device having a catheter with a longitudinal axis and comprising:

an antenna for radiating an electric field having a component in a direction which is tangential to a boundary between said plaque and said inner wall of said artery;

a balloon coupled to the catheter, said balloon having first and second opposing surfaces, wherein said balloon is disposed about said antenna; and a mode filter comprising at least one conductive strip disposed circumferentially around said balloon and concentrically about said longitudinal axis of said catheter for minimizing said electric field component radiated by said antenna in a direction which is tangential to said boundary between the plaque and the artery wall on which the plaque is deposited.

2. The balloon angioplasty device of claim 1 wherein said mode filter is coupled to a first one of said first and second opposing surfaces of said balloon.

3. The balloon angioplasty device of claim 1 wherein said antenna is provided having a helical shape.

4. The balloon angioplasty device of claim 1 wherein said at least one conductive strip includes at least one Z-shaped strip.

5. The balloon angioplasty device of claim 1 wherein said at least one conductive strip comprises a corresponding plurality of spaced conductive strip portions and wherein said at least one conductive strip is a first one of a plurality of conductive strips disposed to provide a plurality of interdigitated strip conductors.

6. A catheter for widening a path through which blood flows in an artery having plaque deposited on an inner wall thereof, the catheter comprising:

a catheter body having a longitudinal axis;

a coaxial cable disposed along said longitudinal axis of said catheter body;

an antenna coupled to a first end of said coaxial cable for radiating an electric field having a component in a direction which is tangential to a boundary between said plaque and said inner wall of said artery;

an inflatable member having an inner surface, an outer surface, an open end and a closed end, wherein said inflatable member is disposed about said antenna and the open end of said member is coupled to said catheter body; and a conductive strip disposed circumferentially around said inflatable member and concentrically about said longitudinal axis of said catheter body on a first one of the inner and outer surfaces of said inflatable member to attenuate said electric field component radiated by said antenna in a direction which is tangential to said boundary between the plaque and said inner wall of said artery.

7. The catheter recited in claim 6 wherein said antenna is provided as a helical antenna.

8. The catheter recited in claim 6 wherein said conductive strip is a first one of a plurality of conductive strips disposed on the first surface of said inflatable member.

9. The catheter recited in claim 8 wherein at least one of said plurality of conductive strips is provided having a Z-shape.

10. The catheter recited in claim 8 wherein each of said plurality of conductive strips comprises a corresponding plurality of spaced conductive strip portions and wherein said plurality of conductive strips are disposed to provide a plurality of interdigitated conductive strips.

11. A heating device, adapted for use with balloon angioplasty techniques for widening a path through which blood flows in an artery having plaque deposited on an inner wall thereof, said device comprising:

a dilation catheter having a longitudinal axis and including a balloon;

a transmission line having at least a portion thereof disposed in said catheter;

an antenna coupled to said transmission line and disposed in the balloon, said antenna radiating an electric field having a component in a direction which is tangential to a boundary between said plaque and said inner wall of said artery; and a mode filter comprising at least one conductive strip disposed circumferentially about said antenna and concentrically about said longitudinal axis of said catheter for minimizing said component of said electric field radiated by said antenna in a direction which is tangential to said boundary between the plaque and said inner wall of said artery.

12. The device of claim 11 wherein:

the balloon is provided from a material which is substantially transparent to electric fields radiated by said antenna and the balloon may be inflated by introduction of a fluid; and said antenna is provided as a helical antenna.

13. The device of claim 12 wherein said mode filter is provided by disposing a conductive material on at least a portion of the balloon.

14. The device of claim 13 wherein said fluid is a first one of a gas or a liquid.

15. The device of claim 14 wherein a dielectric rod is disposed through a central longitudinal axis of said helical antenna.

16. The device of claim 15 wherein said helical antenna is a printed circuit antenna provided by disposing on a first surface of said dielectric rod a conductor in a helical pattern.

17. The device of claim 11 wherein said antenna comprises a dielectric rod having a first end juxtaposed said transmission line and wherein said antenna is a provided as a printed circuit antenna disposed on a first surface of said dielectric rod and said printed circuit antenna is electrically coupled to said transmission line.

18. The device of claim 17 wherein said mode filter is coupled to a first surface of said balloon.

19. A balloon angioplasty device comprising:

a catheter having a longitudinal axis and a channel therein;

an antenna coupled to said catheter for radiating an electric field having a circumferentially radiated component;

a balloon having first and second opposing surfaces, wherein said balloon is coupled to said catheter;

a perfluorocarbon fluid disposed in said balloon such that said perfluorocarbon fluid inflates said balloon and wherein said perfluorocarbon fluid is fed into said balloon through the channel in said catheter; and a mode filter comprising at least one conductive strip disposed circumferentially about said balloon and concentrically about said longitudinal axis of said catheter for minimizing said circumferentially directed electric field component radiated by said antenna.

20. The device of claim 19 wherein said antenna is provided having a helical shape.

* * * * *